United States Patent
McGee et al.

(10) Patent No.: US 6,723,334 B1
(45) Date of Patent: Apr. 20, 2004

(54) BIOLOGICALLY COMPATIBLE BONE CEMENTS AND ORTHOPEDIC METHODS

(75) Inventors: Thomas D. McGee, Ames, IA (US); Marie L. Roemhildt, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 36 days.

(21) Appl. No.: 09/795,452

(22) Filed: Mar. 1, 2001

Related U.S. Application Data

(60) Provisional application No. 60/186,031, filed on Mar. 1, 2000.

(51) Int. Cl.$^7$ .......................... A61F 2/00; C01B 15/16; A01N 59/26; A01N 59/08; A61K 33/14
(52) U.S. Cl. ..................... 424/423; 424/602; 424/665; 424/678; 424/679; 424/680; 424/682; 523/116
(58) Field of Search .............................. 424/422, 423, 424/602, 665, 678, 679, 680, 687, 682, 719; 523/116

(56) References Cited

U.S. PATENT DOCUMENTS

| | | | | |
|---|---|---|---|---|
| 3,787,900 A | * | 1/1974 | McGee | 3/1 |
| 4,655,777 A | * | 4/1987 | Dunn et al. | 632/16 |
| 4,668,295 A | * | 5/1987 | Bajpai | 106/85 |
| 4,737,411 A | * | 4/1988 | Graves | 428/403 |
| 4,943,541 A | * | 7/1990 | Watanabe et al. | 501/10 |
| 5,032,552 A | * | 7/1991 | Nonami et al. | 501/95 |
| 5,246,496 A | * | 9/1993 | Sugama | 106/690 |
| 5,597,383 A | | 1/1997 | Carbone | |
| 5,605,713 A | | 2/1997 | Boltong | |
| 5,635,482 A | * | 6/1997 | Bhatnagar | 514/14 |
| 5,637,412 A | * | 6/1997 | Jennings et al. | 428/703 |
| 5,763,416 A | * | 6/1998 | Bonadio et al. | 514/44 |
| 5,820,632 A | * | 10/1998 | Constantz et al. | 623/16 |
| 5,888,292 A | | 3/1999 | Tremblay | |
| 5,900,053 A | | 5/1999 | Brothers et al. | |
| 6,005,162 A | * | 12/1999 | Constantz | 623/16 |
| 6,034,061 A | * | 3/2000 | Rosen et al. | 514/12 |
| 6,136,029 A | * | 10/2000 | Johnson et al. | 623/16 |
| 6,143,069 A | * | 11/2000 | Brothers et al. | 106/678 |
| 6,149,655 A | * | 11/2000 | Constantz et al. | 606/94 |

OTHER PUBLICATIONS

John Autian et al.; *A Toxicity Profile for Calcium Aluminate*; J Dent Res May–Jun. 1972, vol 51 No. 3.
Dhanjoo N. Ghista; *Biomechanics of Medical Devices*; College of Engineering, Michigan Technological University, Houghton, Michigan; pp. 436–455 (1981).
S. F. Hulbert, et al. *Potential of Ceramic Materials as Permanently Implantable Skeletal Prostheses*; J. Biomed. Mater. Res. vol. 4, pp. 433–456 (1970).
J. J. Klawitter et al.; *Application of Porous Ceramics for the Attachmetn of Load Bearting Internal Orthopedic Applications*; J. Biomed. Mater. Res. Symposium No. 2 (Part 1) pp. 161–229 (1971).
S. F. Hulbert, et al.; *Tissue Reaction to Three Ceramics of Porous and Non–Porous Structures*; J. Biomed. Mater. Res. vol. 6, pp. 347–374 (1972).
S. S. Zasshi; *Study of Root Canal Cements Comprising Calcium Alumnate. First Report on Cytotoxicity*; 1991;29(a):44–54.
B. R. Currell, et al.; *The Acceleration adn Retardation of Set High Alumina Cement by Additives*; Cement adn Concrete Reserach. vol. 7, pp. 420–432, 1987.
S. A. Rodger, et al.; *The Chemistry of Hydration of High Alumina Cement in teh Presence of Accelerating and Retarding Admixtures*; Cement and Concrete Research. vol. 14, pp. 73–82, 1984.
R. N. Edmonds, et al.; *The Hydration of Monocalcium Aluminate at Different Temperatures*; Cement and Concrete Research. vol. 18, pp. 311–320, 1988.
M. R. Nilforoushan, et al.; *The Effect of Additions of Alkaline–Earth Metal Chlorides on the Setting Behavior of a Refractory Calcium Aluminate Cement*; Cement and Concrete Research, vol. 25, No. 7, pp. 1523–1534, 1995.
S. M. Bushell–Watson, et al.; *On the Cause of the Anomalous Setting Behaviour With REspect to Temperature of Calcium Aluminate Cements*; Cement and Concrete Reserch, vol. 20, pp. 677–686, 1990.
M. S. San Juan; *Formation of Chloroaluminates in Calcium Aluminate Cements Cured at High Temperatures abd Exposed to Chloride Solutions*; Department of Materials, Imperial College of Science, Technology and Medicine, London SW7 2BP, UK; pp. 6207–6213 (1997).
H. Pollmann, et al. *Synthesis and Polymorphc Transformations of Solid Solutions in the System*; N. Jb. Miner. Mh. Jg 1988, H.5 193–202.
T. Katsumura; *Viscous Property and Osteogenesis Induction of Hydroxyapatite Thermal Decomposition Product Mixed with Gelatin Implanted into Rabbit Femurs*; Department of Orthopaedic Surgery, Yokohama City University School of Medicine; Accepted Mar. 3, 1998; Biomaterials 19 1998, 1839–1844.
A. Capmas et al., *Effect of Temperature on Setting Time of Calcium Aluminate Cements*, ed. R. J. Mongabhai, Chapman & Hall, 1990, pp. 65–80.
Pöllmann, H.: *Solid Solution of Complex Calcium Aluminate Hydrates Containing Cl, OH, Cl$^-$, OH$^-$ and CO$_3{}^{2-}$ Anions*, Con. Int. Quimica do Cimento, Rio/Brasil, Comm. Theme 2.1, vol. III, (1986) pp. 300–305.

(List continued on next page.)

Primary Examiner—Sreeni Padmanabhan
Assistant Examiner—Lauren Q. Wells
(74) Attorney, Agent, or Firm—Dickstein Shapiro Morin & Oshinsky LLP

(57) ABSTRACT

This invention provides orthopedic cement compositions, containing calcium phosphate component, an anion-donating accelerator to promote rapid setting, and a calcium aluminate component. Further provided are methods for orthopedic repair, including placing the cement at said surgical site by applying low shearing force to said cement to initiate flow.

44 Claims, No Drawings

OTHER PUBLICATIONS

Georg–Michael Darr, et al.; *The Incorporation of Chloride in Calcium Aluminate Hydrates*; Institute fur Gesteinschuttenkunde der Rheinisch–Westfalischer; Communication faite á Mans le 8–12–72, Ind. Chim Belg., 39, No. 7–8, pp. 687–692 (1974).

V.R. Fisher, et al.; *Hydrocalumit: Mischkristalle von "Friedelschem Salz" 3CaO—Al$_2$O$_3$. CaCl2. 10H$_2$O and Tetracalciumaluminat–hydrat 3 CaO. Al$_2$O$_3$ Ca (OH)$_2$ 12H$_2$O?*, pp. 322–334 (1980).

R.N. Edmonds, et al.; *The Hydration of Secar 71 Aluminous Cement at Different Temperatures*; Cement and Concrete Research. vol. 19, pp. 289–294, 1989.

Scott A. Yerby, *Enhancing Adhesion of Bone Cement to Metal Through the use of Coupling Agents*;(visited Feb. 26, 2001) <http://guide.stanford.edu; Feb. 26, 2001>.

*Guidance Document for Testing Orthopedic Bone Cement*; (visited Feb. 26, 2001) <http://www.fds.gov/cdrh/ode/668.html>.

J. Tamura, et al.; *Bone Bonding Ability of Bioactive Bone Cements*; (visited Feb. 26, 2001); <http://koken–db.kogen–db.kogaku.kyoto–u.ac.jp/1998/B/MC/98BMC22006.html>.

*Calcium Chlor*; (visited Feb. 26, 2001); <http://www.usmix.com/Techsheets/Distributor/calcium_chloride/.

G.A. Graves et al.; *Resorbable Ceramic Implants*; Research Institute, University of Dayton; J. Biomed. Mater. Res. Symposium, No. 2 (Part 1) PP. 91/115. 1971.

*Standard Specification for Acrylic Bone Cement*; Designation: F 451–95; pp. 48–53. 1193.

* cited by examiner

BIOLOGICALLY COMPATIBLE BONE CEMENTS AND ORTHOPEDIC METHODS

CROSS-REFERENCE TO RELATED APPLICATIONS

This application claims the benefit of the filing date of the related U.S. provisional patent application Ser. No. 60/186,031, entitled CALCIUM PHOSPHATE COMPATIBLE BONE CEMENTS, filed on March 1, 2000.

FIELD OF INVENTION

This invention relates to biocompatible bone cements and orthopedic methods of use.

BACKGROUND OF THE INVENTION

Orthopedic repairs, required, for instance, as the result of trauma, surgical removal or skeletal changes, are in need of improvement. Existing methods and materials present many unsatisfactory characteristics. Existing orthopedic implants are walled off by the body by a fibrous capsule as the result of the foreign-body protective response of the tissue in contact with the implant. This prevents a strong physical bond between the tissue and the implant. Failure of a joint repair or replacement is often attributed to movement made possible by the presence of the soft fibrous capsule. The capsule gets progressively thicker as the implant ages in the body and the implant becomes more mobile and the motion exceeds a critical level.

Presently, the average service life of a prosthetic implant is about 12 years. About 60% of implants need revision during the lifetime of the patient, subjecting the patient to additional surgery and the risks that accompany such procedures. The success rate is even lower for revision implants. Furthermore, a second revision is often impractical.

Commonly an orthopedic repair includes bone or joint replacement. One important reason for joint replacement is arthritic deterioration that produces pain and loss of mobility and fracture as the result of cartilage and bone deterioration. Another is the result of osteoporetic bone, especially in post-menopausal females, where bone resorbtion produces weak, brittle, and porous bone. Another reason for bone or joint replacement is the deterioration of specific areas of bone resulting from the failure of the circulatory system related to that specific area of bone. When the blood supply is occluded, the loss of blood produces necrotic bone in the affected area. This can lead to bone deterioration and collapse. For example, the spongy bone supporting the articular cortex and cartilage of a proximal femoral head can collapse if its blood supply is lost to disease, injury, or surgical trauma.

Known joint replacements typically incorporate metal, plastic, or ceramic components that are sufficiently biologically-inert that they seldom cause tissue reactions other than the fibrous capsule from the foreign-body response mechanism. A typical hip replacement utilizes a dense polyethylene cup cemented into the reamed acetabulum, and a metal stem cemented into a reamed hole in the femur proximal to the greater trochanter. The ball rotating in the polyethylene cup can be metal, integral with the stem, or ceramic attached to the stem. The metal components are usually a cobalt-chrome alloy, or Titanium $Al_6V_4$ alloy. In animals, it is often 316-L stainless steel. The ceramic ball, and sometimes the cup, can be polycrystalline alumina or, more rarely, a zirconium composition. Failure of these systems is often the result of wear debris; particles of polyethylene and particles of metal often are separated from the prosthetic and invoke an inflammatory response, bone resorbtion, and pain, ultimately resulting in a loosening of the entire prosthesis. This usually occurs within the joint capsule. Wear of the polyethylene is the most common source of the debris. The tissue response includes granulation of tissue by a persistent foreign-body reaction, transforming the articulating capsule into a mass of fibrous tissue that can extend to the ligaments and muscles. Large areas of bone can become poorly vascularized and necrotic. The final stages of deterioration include resorbtion of the supporting bone.

The cement used to attach joint components to surrounding tissue is typically a polymethylmethacrylate (PMMA) cement, which may be modified by chemical additions for radio-opacity or short-term antibiotic activity, for instance. PMMA cements set by an exothermic polymerization reaction. Full strength is obtained quickly, so the cement has the advantage of providing support immediately after setting. The working time and setting time can be controlled to provide the surgeon with a surgically practical cement. It was the development of PMMA cement that made joint replacement possible.

For aged patients with short life expectancy the replacement of "broken hips" with a PMMA-cemented prosthesis was an improvement when it was first invented. For patients having longer lifetimes, there are serious problems as discussed below. The American Society for Testing and Materials specifies the following requirements (ASTM F-451) for PMMA cement:

| | |
|---|---|
| Working time | 5 minutes maximum |
| Setting time | 5–15 minutes |
| Strength | 70 MPa minimum |
| Solubility | 0.05 mg/cm$^3$ maximum |
| Temperature rise | 90° C. maximum |
| Intrusion | 2.0 mm minimum |

The solubility is limited to reduce both local tissue and systemic responses (e.g., when the monomer is distributed systemically it can lower blood pressure and affect organs.). The temperature rise is limited to reduce the cauterization and death of tissue overheated by the exothermic setting reaction. The hazards associated with solubility and temperature rise are well recognized. Other affects are not.

The cement must fill the space between the prosthesis component and the bone. The geometry of the prosthesis component is shaped to aid the load-bearing requirement. The prosthesis-to-PMMA bond and the PMMA-to-tissue bond participate in this. The prosthesis-to-PMMA bond is controlled by the bond chemistry and prosthesis geometry. The PMMA-to-tissue bond is controlled by the tissue reactions and the body's physiological response. Initially this response includes tissue resorbtion and then reconstruction through wound-healing mechanisms to repair the damage produced by the surgical trauma and the temperature rise. When first inserted, the PMMA is smooth and undesirable tissue response is limited. With time, the PMMA becomes rough and brittle, also cracking and releasing fragments. The fragments of cement invoke an inflammatory response in the surrounding tissue and the cracks provide fresh surfaces for chemical exchange. The PMMA is weakened by the cracks. Inflammation and tissue resorbtion further weakens the PMMA-to-tissue bond and, ultimately, failure of the prosthetic device occurs. The most common reason for device replacement is pain, usually occurring with inflammation and device loosening under stress at one of the two bond sites.

Another concomitant problem is that there is no chemical bond between the PMMA and the bone tissue. Instead a mechanical bond is achieved by forcing the fluid PMMA cement, under pressure, into the bone to penetrate pores and irregularities in the bone geometry. Sometimes a dam is inserted in the intramedullary space to restrict the longitudinal flow of the PMMA cement and obtain higher pressure and more radial flow. As an example, the epiphysis region is an important load-bearing area composed of trabecular bone with the trabeculae oriented to transmit the load from one load-bearing region to another. The trabeculae are strong, thin regions of bone, forming the mesh-like interiors of spongy bone, commonly growing along stress lines. Their blood supply comes from the pores (also oriented by the trabeculae orientation) and from the intramedullary region, from attached tendons and from surrounding muscle, although the latter is usually less important. When a blood supply is removed by surgery, it must be compensated by other sources. This is not possible if the pores supplying blood are blocked by the PMMA cement.

Thus, inherent in the use of PMMA cement is an undesirable interference with blood supply. Even in healthy bone, fracture of the hydroxyapatite ("HA") occurs locally and must be repaired or remodeled. Although PMMA cements contribute strength to the bone by filling the pores and supporting the trabeculae, such cements do not have enough strength when the trabeculae become seriously weakened, which is all but inevitable. Therefore the use of PMMA cement presents a basic limitation to the longevity of an implant. The cement breakdown and the PMMA-induced tissue response prevent implants from lasting throughout extended lifespans. The present level of twelve years average life is probably the maximum to be expected.

Another limitation of PMMA cement is the lack of bonding between metal and PMMA cement. A strong bond does exist at the time of surgery, but this declines to zero in about two months. Current practice usually provides a modified surface to obtain mechanical interlocking between the tissue and the prosthesis to attempt to compensate for this deficiency.

Furthermore, in orthopedic implant surgery, an important consideration is the ability of bone to bond to the implant. It is well-known that calcium phosphate in a Ca:P ratio of 1.0 to 2.0 is biocompatible and that bone mineral is an impure HA with a Ca:P ratio of about 1.62. This has led those in the field to investigate bone cements in which HA or modifications of HA are used to form a cement. U.S. Pat. No. 4,612,053 refers to the combination of calcium phosphates with higher and lower Ca:P ratios to produce HA as a cement. Commercial cements are available based on precipitated HA or modified HA. Unfortunately, HA based materials have slow setting times. In addition, although they can fill space and help stabilize, they are too weak and have too low fracture toughness for application as load-bearing members of an implant/tissue or prosthesis/tissue complex. Another limitation of conventional HA cements is their lack of resistance to dilution and their weakening in a bloody environment. This also changes their setting times as well as their strength. There is a need for bone cement capable of transmitting load from tissue to implant.

It would be advantageous for a cement to have the biocompatibility of HA, but the strength and rapid setting characteristics of PMMA cement, making it practical for surgical purposes.

McGee invented a biologically active ceramic material to which bone will bond (U.S. Pat. No. 3,787,900, the entirety of which, is hereby incorporated by reference) and has invented ways to utilize the material to produce strong prosthesis-to-tissue bonding (U.S. patent application Ser. No. 09/146,333). In these inventions, calcium phosphate is combined with an inert structure. The calcium phosphate dominates the tissue response because it is chemically (biologically) active. The inert ceramic structure gives the implant enduring strength; something not possible for calcium phosphates alone because the tissue reactions weaken the calcium phosphate. Magnesium aluminate spinel ($MgAl_2O_4$) is a preferred inert ceramic because it is strong and biocompatible; and because it is stable in contact with the calcium phosphate when fired at high temperatures. The calcium phosphates are salts of a strong base, $Ca(OH)_2$, and a weak acid $H_3(PO_4)$. So is magnesium aluminate spinel. This unique combination of a calcium phosphate and an inorganic, insoluble salt as a fired, composite ceramic, makes an implant that is structurally strong and that invokes positive tissue response. It would be advantageous for orthopedic cements to accomplish this same purpose, incorporating the calcium phosphate for tissue response with strong hydraulic cements to produce a product that has the same advantages as the fired ceramic of the McGee patent but that is a cement instead of a solid ceramic.

BRIEF SUMMARY OF THE INVENTION

The present invention provides bone cement compositions and methods for use in surgery and other medical procedures. The bone cement compositions of the invention are biocompatible, fast setting, strong, and extremely durable, making them practical for use in prosthesis, implant, and other surgical procedures. This new bone cement includes calcium phosphates, which were previously thought to be undesirable in such compositions because of their effect of reducing cement strength. In accordance with this invention, the calcium phosphate enhances the cement's biocompatibility and the cement bond strength is enhanced by using one or more other biocompatible cements, e.g., calcium aluminates, together with accelerators, to produce strong, biologically active cement compositions suitable for replacing polymethylmethacrylate (PMMA) cements. The new bone cements stimulate bone growth and mineralization, are not walled off by the body's foreign-body defense mechanisms, and preferably do not penetrate the pores of bone so as not to block the bone's blood supply. The cement compositions according to the invention also provide excellent bonds to tissue and to metal.

The setting mechanisms of the cement compositions of the invention are controlled with an accelerator that controls the working and setting times. Relatively high accelerator concentrations are preferably used such that the setting mechanism incorporates the accelerator's anions into the calcium aluminate bonding phase to produce a new calcium anion-aluminate bond not used before in bone cements.

The bone cements can be readily manipulated during surgery or other medical procedures with placement techniques superior to those found in the prior art. The cement is preferably dilatent, and thus will not readily mix with body fluids such as blood. The cement is preferably fabricated to only flow under the influence of low shearing force, e.g., vibration, making it possible to place the cement and obtain high strength in bonding to bone while extensive penetration of bone pores is avoided. The cement can also be formulated in a more conventional fluid state or as a thixotropic fluid.

The inorganic bone cements of the invention have the necessary working properties for placement during surgery. This includes new methods of placement because the preferred inorganic cements do not flow in the same way organic cements flow.

The new cements contain calcium phosphates that stimulate bone growth and mineralization. They are not walled off by the foreign-body defense mechanism because the chemistry of interaction with the tissue is dominated by the calcium phosphate component. Because pure calcium phosphate cements are weak, however, the strength is supplemented by using one or more other biocompatible cement phases as a part of the composition. The calcium phosphate component can be present as a chemically reactive component participating in the cement bond, or as an unreactive component in the setting reaction but as a reactive component with the tissue. Also, in some compositions, part of the calcium phosphate may participate in the cement reaction and part may serve the tissue reaction function. All these bonding phases are biocompatible.

Calcium aluminate cements can be used in conjunction with calcium phosphates to produce a strong, biologically active cement suitable to replace PMMA cement in bonding prostheses. This cement will be generally useful as a bone cement because it contains calcium phosphate that dominates the tissue response, because it is strong enough for load-bearing applications to stabilize bone, and because it bonds to bone and to metal. It also can be used in other bone support or replacement situations because it is strong and biocompatible. These new cement compositions are strong enough and biocompatible enough to be used in repairing fractures and for other orthopedic applications. The new cement compositions can be combined with various prosthesis designs, with aggregates, and with reinforcing composite materials. All such applications are included in the scope of this invention.

To one skilled in the art of orthopedic surgery, the biocompatible, strong, bone cements of the invention have many applications and methods available to implement the applications. These include cementing bone fragments together to make a structural whole, incorporating various sizes of calcium phosphate or other bodies in the cement for structural and biological reasons, using fibers, wires, nets or rods to reinforce the cement (this can be similar to reinforced concrete where the reinforcement improves tensile strength), using the cement between metal components and irregular bone (an example is using it to fill the space between an irregular tibia and the tibia tray of a knee implant), cementing prosthesis components together, and as a strong covering to strengthen weak or osteoporitic bone. All such applications are within the scope of this invention.

The above-described and other advantages and characteristics of the invention will be more readily understood upon a reading of the Detailed Description of the Invention.

DETAILED DESCRIPTION OF THE INVENTION

Reference will now be made in detail to preferred embodiments of the invention, which together with the following examples, serve to sufficiently describe and explain the principles of the invention so as to enable one of ordinary skill in the art to make and use the invention.

As expressed above, there is a need in the field of orthopedic surgery for cements that are biologically-active, and yet practical for surgery in terms of working time, setting time, strength, solubility, temperature rise, and intrusion. Heretofore, the development of such a cement has not been accomplished. This invention relates to such cement compositions containing a calcium phosphate component and a calcium aluminate component, preferably with an accelerator. The accelerator should be able to donate chlorine or other anions to the bond phase reaction of the cement composition. These new bone cement compositions have the beneficial characteristics of PMMA cement, which are necessary to make the cements surgically practical, plus they are biologically-active so as to produce a positive tissue response.

Calcium aluminate cements have been used as high early strength cements to replace Portland cement in ordinary concrete structures, including piers for sea water installations. Body fluids typically have salt concentrations much like sea water. The calcium aluminate cements are termed "high early strength" because they only take hours to reach high strength, compared to days for Portland cements. However, orthopedic cements must set in a matter of minutes to be practical for surgery.

Calcium aluminates can be biocompatible and resorbable, but the tissue response depends on the $CaO:Al_2O_3$ ratio ("C:A ratio"). The higher ratio compounds have greater solubility. C:A ratios significantly lower than about 1:1 produce cements that are only slightly soluble in the body. Such compounds encourage tissue in-growth and replacement.

Calcium aluminate cements can be made to set more rapidly by adding chemicals known as accelerators, which act as electrolytes or as heterogeneous nucleating agents. Use of accelerators is known in the art of ordinary cements, such as Portland cement, discussed above. Many different compounds such as lithium chloride, acetic acid, calcium chloride, calcium sulfate hemi-hydrate, citric acid, and magnesium chloride are useful as accelerators to expedite setting in the cement compositions of the invention. These are usually effective at about 0.5%. Three to five percent calcium sulfate hemi-hydrate is also used, but such an amount is not suitable for implant cement because the cement is too soluble. In general, calcium phosphates have tended to retard or prevent set; the calcium aluminate and accelerator-containing cement compositions of the invention avoid this problem.

Rapid set time and high attained strength occurs at a C:A ratio of about 1:1. A relatively high concentration of an accelerator, such as sodium chloride (NaCl), lithium chloride (LiCl), magnesium chloride ($MgCl_2$), aluminum chloride ($AlCl_3$), potassium chloride (KCl), or calcium chloride ($CaCl_2$), is preferably added to the cement composition so that the chlorine ion from the accelerator participates in the setting reaction by producing a new chemical: a hydrated calcium chloro-aluminate which becomes the bond phase, instead of the usual hydrated calcium aluminate phase which would occur without the anion containing accelerator. The preferred accelerators contain a compound that can donate an anion, such as the chlorine ion described above, that can fit into the calcium aluminate hydrate structure during the bond phase to form a stable compound. Metal anions from the halide group are particularly suitable for this purpose.

The accelerators can be added as powder or in solution. The preferred accelerator is a calcium chloride ($CaCl_2$) aqueous solution of between about 0.5 and 4.0 molar, which will donate chlorine ions to the bonding reaction. The cement compositions of the invention provide setting times and working times comparable to PMMA (as described above). They also have high, enduring strength, at least equal to, if not greater than, that of PMMA cement. The preferred concentration of $CaCl_2$ in aqueous solution is about 2 molar. Combinations of $CaCl_2$ with NaCl or other accelerators are also effective.

Adding calcium phosphates to calcium aluminate cements prior to this invention was extremely problematic because the cements did not set, were weak, or lost strength in only a few weeks. In accordance with this invention, by replacing the calcium aluminate bond with the anion-modified calcium aluminate bond described above, it is possible to combine the calcium aluminate cement with calcium phosphates and maintain the necessary properties of setting time, working time, rapid strength rise, and enduring strength necessary to make the cement practical for surgical purposes. The calcium phosphate component gives the cement bioactivity similar to that of the fired osteoceramic described in U.S. Pat. No. 3,787,900 to McGee, described above.

The cement compositions in accordance with this invention preferably comprise about 40 to 70% by weight calcium aluminate, about 15–50% by weight calcium phosphate, and about 1.5 to 8% by weight calcium chloride. More preferably the cement composition comprises about 50 to 65% by weight calcium aluminate, about 20 to 35% by weight calcium phosphate, and about 3 to 6% by weight calcium chloride. Aggregates can also be added to such compositions to reinforce the cement or to improve the positive biological response. In a preferred embodiment, the cement composition includes about 63% by weight calcium aluminate, about 31.5% by weight beta tricalcium phosphate, and about 5.5% by weight calcium chloride.

The preferred bone cement of this invention, when maintained at body temperature, 37° C., in simulated body solution (Lactated Ringer's solution), attains a rapid increase in strength, being as strong as PMMA cement in only a few hours and continuing to gradually increase in strength for many months. In accordance with the invention, the biocompatible cement meets or exceeds the standards required for PMMA cement, including: a working time of about 5 to 20 minutes or better, a setting time of about 5 to 30 minutes or better, an attained strength of at least 70 MPa and preferably over 100 MPa, appropriate solubility, a temperature increase of less than 90° C. and preferably less than about 30° C., and an intrusion of no more than about 2.0 mm. These characteristics make the bone cement desirable for surgical purposes.

In accordance with the invention, the preferred cement is as strong or stronger than necessary to provide a suitable orthopedic cement for prosthetic implants. As evidence of this, experimental results were obtained under the following scenario: metal rods, simulating the femoral component of a typical hip replacement, were cemented into femurs from canine cadavers. After setting for various times, the rods were removed using an Instron mechanical testing instrument at a strain rate of 1 mm/min. All the experiments exhibited failure at the rod/cement interface, not within the cement or at the cement/tissue interface. The cement-to-metal bond was stronger than the expected load (3 to 6 times the body weight for any given subject) for all experiments in which the cement set longer than four hours when stored at 37° C. and 100% humidity (internal body conditions). As observed, the strength of the cement of the invention is maintained or even increased over time, whereas that of PMMA cement declines to zero eventually.

The preferred cement compositions of the invention have flow characteristics allowing for precise placement of the cement at a surgical site, and also provide the advantage of allowing for a cement that does not impede blood flow to the bone, thus avoiding the necrotic deterioration inherent in the prior art. The conventional PMMA cements are forced into the prepared surgical site, and into the cells of the surrounding trabecular bone, by exerting high pressures. The amount of pressure applied with hand-held guns, the degree of polymerization, and other factors affect the flow properties, but the flow is generally Newtonian. (The shear resistance of PMMA is a linear function of the flow rate.) However, in accordance with the invention, flow characteristics of the calcium phosphate-calcium aluminate cement compositions can be controlled by using deflocculating agents, or surface active agents. Examples of useful charge-dominated deflocculants are sodium carbonate, tetrasodium pyrophosphate, ammonium hydroxide, etc., which have an alkali ion that is attracted to the surface. Examples of useful steric deflocculants include sodium and ammonium polyacrylates, sodium silicate, and other polyanion molecules.

The preferred flow characteristics of the cement compositions are dilatent, i.e., the cement will flow under gentle vibrational influence; however, under more extreme shear, pressure, or stress, the cement acts as a solid. The dilatency results from the packing of the particles of the cement. Agitation of the composition, if forceful enough, will increase its volume, but if there is insufficient water to allow for the motion of the particles over one another, then the composition will resist shear. Thus, the flow characteristics of the cement compositions according to the invention can be controlled to aid in placement of the cement at the surgical site. The cements can also have thixotropic flow characteristics, meaning that the cement will flow as a liquid under the influence of shearing forces, but will remain as a solid or gel when at rest (i.e., not subject to shear forces).

Because the strength of hydraulic cements is dependent on the water-to-cement ratio, and such cements are strongest at low ratios, it is preferred to use a relatively small amount of water. The flow characteristics can be further controlled by particle size distribution, and by concomitantly using deflocculating agents as described above. Controlling these parameters and using a relatively high concentration of accelerator with a minimum of water achieves the desired physical properties and also, dilatent flow. Control of flow is achieved by control of the particle size distribution and can be manipulated by tailoring the particle size of both the calcium aluminate and the calcium phosphate. For rapid setting, the cement particles preferably should be finer than 100 $\mu$m.

The cement compositions of the invention are preferably ground finely so that some or many of the particles are fine enough to exhibit colloidal properties. The deflocculating agents, of course, help to prevent flocculation of these fine particles. This makes it possible to further reduce the amount of water required. By selecting the particle size and deflocculants, one can obtain a Newtonian fluid, a dilatent fluid, or a thixotropic fluid. Any of the three can be suitable for different surgical purposes. Nearly Newtonian flow can be achieved with sodium polyacrylate deflocculant. Thixotropic flow occurs when partial deflocculation is used, utilizing less deflocculating agent. Dilatent flow occurs when the grain size distribution of the cement allows close packing of particles and a minimum of water content. One of ordinary skill in the art can fabricate various biocompatible cements for different orthopedic purposes and flow requirements given the teachings herein.

The preferred particle size distribution is such that the composition has enough fine particles for deflocculation and flow, but that packs together in such a way so at to require a minimum of water. Adding very fine particles also enhances flow characteristics, like miniature ball bearings between larger particles. In Example 5 below, it is shown how the particle size of the cement composition can be varied to tailor the setting time and strength characteristics of the resulting cement.

Dilatent flow has advantages for placement in various surgical situations. The dilatent cement compositions according to the invention appear to be rigid, wet masses at rest. However, they flow readily if low shearing forces are applied with, for example, vibration. This makes it possible to control the placement of the cement because as soon as the shear forces are stopped the cement ceases flowing.

New placement procedures for the cement of the invention allow superior placement of the cement to bond to prostheses, to bone, and to not block the blood supply of the tissue supporting the structure. This is desirable for maintaining healthy bone in contact with the cement. These placement procedures include preparation of the surgical site, placement of the cement at the surgical site, and installation of the prosthesis, using a low shearing force, such as vibration, to control the flow of the cement. Preparation of the surgical site depends on the particular surgical procedure. For example, for installation of a hip replacement joint, the stem of a metal femoral component is cemented in place. The surgeon cuts off the femoral stem and reams a hole in the center of the remaining bone to allow the cement and the stem to be inserted. The surgeon injects the cement and then drives the stem into place. Prior to injection, the cement will have been injected into a tube by vibration. Then the cement is transferred from the tube into the bone cavity, holding its shape during insertion as it is pushed out of the tube. The stem of the prosthesis is then positioned into the cement by vibrating the prosthesis. As the stem is inserted, the excess cement will extrude from the bone and is removed. The preferred procedure results in about one millimeter of cement between the bone and the stem at all locations.

As discussed above, one weakness of convention PMMA cements is their rapid exothermic chemical reaction which produces temperatures high enough to cauterize surrounding tissue. This weakness of the prior art is overcome by the invention. The preferred calcium phosphate-calcium aluminate cement compositions do not release energy as rapidly. During setting of the preferred cements, the temperature can rise due to exothermic reaction to about 45° C. when mixed at room temperature (25° C.). This temperature rise of about 20° C. is not great enough to be harmful to the surrounding tissue. A temperature rise of up to 40° C. is suitable for the cements of the invention.

Also, in accordance with the invention, the preferred cement compositions do not penetrate the pores of the bone tissue. Prosthesis implanted in, for example, osteoporotic bone, should distribute the load over a larger bone area to reduce the local stresses to less than the fracture stress. If the cement in contact with the tissue stimulates bone repair, this will also improve the ability for the bone to support the load. If the cement in contact with the tissue has flow characteristics so that it will not penetrate trabecular pores of the bone, the pores will not be filled in depth, and so the blood supply will not be blocked. The preferred cement compositions of this invention do not cut off blood supply to the bone and, therefore, bone growth is not stunted, but instead is promoted by the calcium phosphate component of the cement. Production of necrotic bone is diminished through use of these cements.

The new cement compositions can be combined with various biocompatible aggregates, such as, but not limited to, osteoceramics, bone fragments, or calcium phosphate grains. These aggregates serve to improve the biological response of tissue and the mechanical properties of the cement composite. Use of aggregates includes cementing bone fragments together to make a structural whole, incorporating various sizes of calcium phosphate or other bodies in the cement for structural and biological reasons; this can be similar to ordinary concrete where the aggregates increase strength and better distribute load. The cement can be used between metal components and irregular bone (an example is using it to fill the space between an irregular tibia and the tibia tray of a knee implant), cementing prosthesis components together, and as a strong covering to strengthen weak or osteoporitic bone. The use of biocompatible aggregates promotes the positive tissue response and helps to prevent the development of necrotic bone described above by inhibiting penetration of the tissue pores by the cement composition as discussed above.

Examples 2–9 below are illustrative of features of cement compositions in accordance with the invention. Example 1 below shows that calcium phosphate weakens calcium aluminate cement without the addition of an anion contributing accelerator.

EXAMPLE 1

Calcium carbonate and aluminum oxide in the ratio of 5:7 were ground together in a ball mill, transferred to a crucible and fired at 1450° C. to produce a melt. The crucible was removed from the furnace, cooled rapidly, and the clinker was crushed and ground with a ball mill to produce a powder that would pass a 75 $\mu$m sieve. This was mixed with water to a smooth paste consistency and poured into a mold. The setting time was over an hour. Four percent calcium sulfate hemihydrate was mixed with the powder and the setting time was reduced to 20 minutes.

The mixture was then combined with various amounts of tricalcium phosphate, tempered with water to make a fluid paste, and poured into a mold to produce cylinders, ½inch diameter by ½inch high. These were stored in a humid atmosphere. At 12 minutes, one day, and one week the cylinders were tested with a mechanical testing instrument for strength. The maximum crushing strength was only eight MPa at seven days. Without the calcium phosphate the strength was 65 MPa.

EXAMPLE 2

Powdered calcium aluminate of approximately 1:1 calcium-to-alumina ratio was combined with various accelerators. Sodium chloride (NaCl), lithium chloride (LiCl), citric acid, and calcium chloride ($CaCl_2$), were added at very low concentrations, about 0.125 to 1%. Generally, they acted as accelerators at very low concentrations but became retarders at the higher concentrations. The shortest setting times were much too long to be practical for surgery. Strength did not become appreciable for about an hour. The optimum concentration varied but was usually a fraction of one percent. We discovered, however, that at much higher concentrations (over 1%) they were effective as accelerators. When about 1.5 to 8% calcium chloride was added, the working time and setting time were about ten minutes and 20 minutes respectively. Other chlorides such as mixtures of lithium chloride and sodium chloride were equally effective. The working time and the setting time was controllable.

EXAMPLE 3

Using a 2.0 molar calcium chloride solution to obtain a working consistency of chloride accelerator, an approximately 1:1 ratio calcium aluminate cement was combined with a calcium phosphate having a Ca:P ratio between about 1:1 to about 2:1. Ten grams of dry material were mixed for one minute with enough liquid to produce a fluid paste. The mixture was cast into molds and allowed to set. After twenty minutes the molds were removed and the specimens were placed in vials containing Lactated Ringer's solution at 37° C. for one week. The setting times varied from 8 to 40 minutes. The crushing strength was a function of the calcium phosphate concentration, as follows:

| Percent Calcium Aluminate | Percent Calcium Phosphate | Crushing Strength MPa |
|---|---|---|
| 100 | 0.0 | 97.0 |
| 90 | 10 | 81.8 |
| 80 | 20 | 77.3 |
| 70 | 30 | 94.8 |
| 60 | 40 | 24.4 |
| 50 | 50 | 40.2 |
| 40 | 60 | 28.3 |
| 30 | 70 | 11.3 |
| 20 | 80 | 0.9 |

The strength was reduced as the calcium phosphate concentration was increased.

EXAMPLE 4

Calcium aluminate of about 1:1 C:A ratio was combined with five different types of calcium phosphate as shown in the Table below. β-TCP is beta tricalcium phosphate; TCP-w is beta tricalcium phosphate mixed with some alpha tricalcium phosphate; TCP is a very fine mixture of tricalcium phosphate with a C:P ratio of 1.62; TCP-f is the same mixture as TCP, but with a coarser grain size; and OC is osteoceramic prepared in accordance with the McGee patent (U.S. Pat. No. 3,787,900). The powders were mixed together, with accelerator, and water was added. Working and setting times were determined and compressive strength at 1 week was measured. The results were as follows:

TABLE

Effect of calcium phosphates on calcium aluminate cements

| ID | CA (gr.) | CP type | (gr.) | solution/ powder | WT (min.) | ST (min) | CS (MPa) 1-week | (n) |
|---|---|---|---|---|---|---|---|---|
| 1 | 10.00 | β-TCP | 5.0 | 0.31 | 11 | 24 | 63–110 | 6 |
| 1b | 10.00 | β-TCP | 2.5 | 0.33 | 10 | 26 | 91–138 | 6 |
| 2 | 10.00 | TCP-w | 5.0 | 0.27 | 20 | 30 | 79–100 | 6 |
| 2b | 10.00 | TCP-w | 2.5 | 0.28 | 10 | 19 | 76–116 | 6 |
| 3 | 10.00 | TCP | 5.0 | 0.47 | 30 | 60 | 10–22 | 6 |
| 3b | 10.00 | TCP | 2.5 | 0.36 | 21 | 55 | 65–93 | 5 |
| 4 | 10.00 | TCP-f | 5.0 | 0.31 | 9 | 30 | 53–79 | 5 |
| 4b | 10.00 | TCP-f | 2.5 | 0.33 | 11 | 20 | 47–81 | 6 |
| 5 | 10.00 | OC | 5.0 | 0.35 | 9 | 18 | 60–103 | 6 |
| 5b | 10.00 | OC | 2.5 | 0.34 | 10 | 18 | 52–88 | 6 |

Note that the setting time and strength depended on the particular calcium phosphate.

EXAMPLE 5

Part of the effect of the calcium phosphates is chemical and part is from the particle size. This example uses a ground osteoceramic: 50 volume percent tricalcium phosphate and 50 volume percent magnesium aluminate spinel as the source of calcium phosphate (see U.S. Pat. No. 3,787,900). It illustrates the effect of particle size on cold strength (CS) and setting time (ST). It also shows one example that these cements can be used with aggregates made from the osteoceramic or other materials to produce other products based on the cement compositions in accordance with the invention.

Calcium aluminate and osteoceramic powders were mixed. A 2.0 molar calcium chloride solution was added and mixed for 1 minute to form a cement paste. Cement specimens were prepared following the method described previously. The coarser aggregate gave shorter setting time and slightly smaller strength. The setting and average. compressive strength after 24 hours is given below.

| | CA wt % | OC wt % | P.S.- OC | s/c | ST (min) | CS (MPa) | S.D. | (n) |
|---|---|---|---|---|---|---|---|---|
| 1 | 50 | 50 | −100 +200 | 0.50 | 20 | 63.5 | 5.6 | 4 |
| 2 | 50 | 50 | −65 +100 | 0.50 | 15 | 60.3 | 7.4 | 4 |
| 3 | 50 | 50 | −30 +48 | 0.50 | 12 | 50.7 | 7.5 | 4 |

P.S. is the particle size of the OC given as sieve sizes. For example, −100 +200 means the particles would pass through a 100 mesh standard sieve, but would be retained by a 200 mesh sieve.

EXAMPLE 6

One of the requirements for surgically practical cement is enduring strength. After discovering ways to accelerate the set, control the particle size, prevent the calcium phosphate from interfering with cement setting reactions and obtaining high strength, we measured the strength as a function of time.

An approximately 1:1 (C:A) ratio calcium aluminate and β-tricalcium phosphate powders were combined and cement was prepared by adding a 2 molar calcium chloride accelerator solution to give adequate flow for molding. The composition was 63.5% by weight of calcium aluminate powder, 31.5% by weight tricalcium phosphate powder, and 5.5% calcium chloride. This composition was mixed with 24.3% by weight deionized water. The cement was mixed for 1 minute and then placed in acrylic molds. Specimens were removed from the molds 20 minutes after setting. Specimens were placed in vials with Lactated Ringer's solution and stored at 37° C. until testing. The average strength was over 100 MPa at 1 week and did not change significantly as measured up to 32 weeks. The results were as follows:

TABLE

Compressive strength over time

| Time | CS (MPa) | S.D. | (n) |
|---|---|---|---|
| 1 hr | 30.34 | 2.49 | 11 |
| 4 hr | 71.26 | 5.98 | 12 |
| 12 hr | 77.94 | 12.02 | 12 |
| 24 hr | 71.73 | 8.01 | 12 |
| 24 hr | 74.73 | 5.22 | 12 |
| 48 hr | 66.16 | 7.61 | 11 |
| 5 days | 92.27 | 16.31 | 10 |
| 1 wk | 105.91 | 12.77 | 9 |
| 4 wk | 111.56 | 12.94 | 11 |
| 8 wk | 98.11 | 18.53 | 10 |

TABLE-continued

Compressive strength over time

| Time  | CS (MPa) | S.D.  | (n) |
|-------|----------|-------|-----|
| 16 wk | 107.53   | 21.48 | 11  |
| 32 wk | 99.71    | 14.93 | 11  |

EXAMPLE 7

Experiments with wetting agents and accelerators made it possible to obtain control of the theological properties. Desirable properties were found to include placement of the cement in cavities in the tissue in which the flow characteristics could be controlled at the time of surgery. The cement described in Example 6 has the advantageous flow characteristics as described here.

Flow of the cement was measured using a procedure from T. Katsumura, T. Koshino and T. Saito, "Viscous Property and Osteogenesis Induction of Hydroxyapatite Thermal Decomposition Product Mixed With Gelatin Implanted Into Rabbit Femurs," Biomaterials: 19, (1839–1844), 1998 (incorporated by reference herein) to measure the flow of calcium phosphate cements without the use of vibration. The procedure was modified by including the effects of vibration to control the flow. A disc of cement of standard amount was placed between two glass boards and a standard load of 120 grams total vertical mass was applied. Vibration was applied to the cement immediately after placement for three different times: 15, 30, and 45 seconds. The diameter of the cement disc was measured in three locations initially, immediately after vibration, and at 5, 10, 15, and 20 minutes. The results were as follows:

|         | Diameter (cm) |          |          |          |
|---------|---------------|----------|----------|----------|
| Time    | Control       | V-15 sec | V-30 sec | V-45 sec |
| Initial | 0.986         | 0.938    | 1.165    | 0.986    |
| After vib | n/a         | 4.883    | 6.041    | —        |
| 5 min   | 1.274         | 4.995    | 6.111    | 6.170    |
| 10 min  | 1.371         | 5.006    | 6.143    | 6.508    |
| 15 min  | 1.390         | 5.008    | 6.150    | 6.534    |
| 20 min  | 1.395         | 5.038    | 6.150    | 6.532    |

(10 specimens were used for each value)

When vibration was applied, the overall flow of the cement increased greatly, with most of the flow occurring during the first few seconds of vibration. Without 1vibration, very little flow occurred. Again, with the onset of vibration, the flow increased. Very little flow occurred in any of the specimens after vibration stopped. The difference in flow is greater than appears from the raw numbers because the area of flow is proportional to the square of the diameter. Therefore a change of a diameter of 1.395 to 6.932 is equivalent to a flow area change from 1.53 to 37.8 $cm^2$. Controlling the amplitude and time of vibration can be used to control placement.

EXAMPLE 8

Example 8 refers to the cement discussed in Example 6. An advantageous quality of an orthopedic cement is sufficient bond to metal components of implants to support the load and give enduring strength. Simulated implant experiments were performed in which a polished 316-L stainless steel rod was cemented into the reamed femur medulla of canine cadavers. After four hours the resistance to tensile withdrawal was measured with and Instron mechanical testing instrument. The bond to the metal rod was less than the tissue-to-cement bond or the internal cohesion of the cement. The interfacial shear strength of the cement-to-metal bond was greater than 1 MPa for all specimens. This is more than enough to support the weight of a patient under real implant conditions. The strength did not change in 60 days when similar experiments were conducted using a polyvinyl cylinder instead of the femur.

EXAMPLE 9

Example 9 refers to the cement from Example 6. Large holes, especially irregular holes in curved areas, need a structure that fits that area. These experimental results show one way this is satisfied. Beads of calciumphosphate/spinel were manufactured according to the McGee patent (see U.S. Pat. No. 3,787,900). They were strung on non-absorbable, mono-filament sutures to make the woof for a loom. Non-absorbable, mono-filament sutures were used to make the warp for the loom. A bead-net cloth was woven. The exterior surface of the cloth was dominated by the beads.

An irregular defect was made in the skull of a dog, comprising about 25% of one the side of the cranium. A gel was placed on the skull to form a negative mold. A plaster-of-Paris model was made from the mold. The bead cloth was cut to fit the irregular hole and put in place on the model. The cement was smeared smoothly over the irregular surface, filling the gaps between the beads and stabilizing them. After setting, a permanent implant resulted that fit the defect. The bead net prosthesis was lifted off the model and the cement was smoothed on the underside to produce a stronger, smoother prosthesis. After it hardened, the prosthesis was placed in the defect of the skull, attaching it with non-absorbable sutures previously bonded in the same cement.

The foregoing description and examples are illustrative of exemplary embodiments which achieve the objects, features and advantages of the present invention. It should be apparent that many changes, modifications, substitutions may be made to the described embodiments without departing from the spirit or scope of the invention. The invention is not to be considered as limited by the foregoing description or embodiments, but is only limited by the construed scope of the appended claims.

What is claimed as new and desired to be protected by letters patent of the United States is:

1. An orthopedic cement composition, comprising:
    a calcium phosphate component in an amount of about 5% to 70% by weight;
    a hydraulic calcium aluminate component in an amount of about 40% to 70% by weight;
    a chlorine accelerator component in an amount of about 1.5% to 8% by weight to promote setting of said hydraulic calcium aluminate component in less than about 30 minutes; and
    wherein said chlorine component donates an anion to produce a calcium chloro-aluminate bond in said cement.

2. The orthopedic cement composition of claim 1, wherein said accelerator is selected from the group consisting of lithium chloride, calcium chloride, sodium chloride, potassium chloride, aluminum chloride, and magnesium chloride.

3. The orthopedic cement composition of claim 1, wherein said accelerator is calcium chloride.

4. The orthopedic cement composition of claim 3, wherein said calcium chloride is an aqueous solution of between about 0.5 to 4.0 molar concentration.

5. The orthopedic cement composition of claim 1, wherein said accelerator is added as a powder.

6. The orthopedic cement composition of claim 5, wherein said accelerator comprises calcium chloride.

7. The orthopedic cement composition of claim 1, wherein the calcium phosphate component has a Ca:P ratio of between about 1:1 and about 2:1.

8. The orthopedic cement composition of claim 1, wherein the calcium aluminate component has a Ca:Al ratio of between about 0.5:1 and about 2:1.

9. The orthopedic cement composition of claim 1, comprising about 63% by weight calcium aluminate, about 31.5% by weight beta tricalcium phosphate, and about 5.5% by weight calcium chloride.

10. The orthopedic cement composition of claim 1, wherein prior to solidification the composition flows only when subjected to a shearing force.

11. The orthopedic cement composition of claim 1, wherein the composition attains a compressive strength of at least about 70 MPa.

12. The orthopedic cement composition of claim 1, wherein the composition attains a compressive strength of over 100 MPa.

13. The orthopedic cement composition of claim 1, wherein the composition attains a cement-to-metal bond having an interfacial shear strength of at least about 1 MPa.

14. The orthopedic cement composition of claim 1, wherein said composition has a working time between about 5 to about 20 minutes.

15. The orthopedic cement composition of claim 1, wherein said composition has a setting time between about 5 to about 30 minutes.

16. The orthopedic cement composition of claim 1, wherein during setting reactions the composition produces an internal temperature rise of not greater than about 40° C.

17. The orthopedic cement composition of claim 1, further comprising a deflocculating agent.

18. The orthopedic cement composition of claim 17, wherein said deflocculating agent is selected from the group consisting of sodium carbonate, tetrasodium pyrophosphate, ammonium hydroxide, sodium polyacrylate, ammonium polyacrylate, and sodium silicate.

19. The orthopedic cement composition of claim 1 having an average particle size of less than about 100 $\mu$m.

20. The orthopedic cement composition of claim 1, further comprising aggregates containing calcium phosphate.

21. The orthopedic cement composition of claim 20, wherein said aggregates comprise calcium phosphate having a Ca:P ratio of about 1:1 to about 2:1.

22. The orthopedic cement composition of claim 20, wherein said aggregates inhibit said cement composition from penetrating into tissue pores.

23. A biologically active inorganic cement comprising:
   about 5 to 70 weight % calcium phosphate having a Ca:P ratio of about 1:1 to about 2: 1;
   hydraulic calcium aluminate having a Ca:Al ratio of about 0.5:1 to about 2:1; and
   an aqueous accelerator solution containing about 0.5 to 4.0 moles of $C_2$ ions per liter, at least some of said $Cl_2$ ions of said accelerator being incorporated in a bonding phase during the setting reaction of the cement to produce a calcium chloroaluminate bond.

24. The cement of claim 23, wherein said accelerator comprises calcium chloride.

25. The cement of claim 23, wherein said cement flows as a liquid upon the application of vibrational energy.

26. The cement of claim 23, wherein said cement has a compressive strength of over about 70 MPa.

27. The cement of claim 23, wherein said cement is in the form of a prosthetic device.

28. The cement of claim 23, wherein during setting reactions said cement produces an internal temperature rise of not greater than about 40° C.

29. The cement of claim 23, wherein said cement comprising calcium phosphate, hydrated phases of said calcium aluminate component, including hydrated calcium chloroaluminates from said accelerator, is bound to a metallic prosthetic device by an interfacial shear-strength of at least about 1 MPa.

30. The cement of claim 23, wherein said cement comprises about 40 to 70% by weight calcium aluminate, about 20 to 50% by weight calcium phosphate, and about 1.5 to 8% by weight calcium chloride.

31. The cement of claim 23, in the form of a composite comprising a material selected from the group consisting of fibers, wires, nets, or rods to reinforce the cement.

32. The cement of claim 23, further comprising a deflocculating agent.

33. The cement of claim 32, wherein said deflocculating agent is selected from the group consisting of sodium carbonate, tetrasodium pyrophosphate, ammonium hydroxide, sodium polyacrylate, ammonium polyacrylate, and sodium silicate.

34. The cement of claim 23, having an average particle of size of less than about 100 $\mu$m.

35. The cement of claim 23, further comprising aggregates containing calcium phosphate.

36. The cement of claim 35, wherein said aggregates comprise calcium phosphate having a Ca:P ratio of about 1:1 to about 2:1.

37. The cement of claim 35, wherein said aggregates inhibit said cement composition from penetrating into tissue pores.

38. A method for orthopedic repair, comprising:
   placement of a cement according to claim 1 at said surgical site; and applying vibration to said cement to initiate flowing of said cement.

39. The method of claim 38, wherein said orthopedic repair comprises installing a prosthetic apparatus.

40. The method of claim 38, wherein said cement is in the form of a composite comprising a material selected from the group consisting of, biocompatible aggregate, fibers, wires, nets, or rods.

41. The method of claim 38, wherein said repair comprises filling holes joint replacement.

42. The method of claim 38, wherein said orthopedic repair comprises joint replacement.

43. The method of claim 38, wherein said orthopedic repair comprises applying said cement to stabilize a woven bead net cloth comprising beads containing calcium phosphate strung on non-absorbable sutures.

44. The method of claim 38, wherein said beads of said bead net cloth comprise calcium phosphate.

* * * * *